(12) United States Patent
Ogawa

(10) Patent No.: US 6,644,809 B2
(45) Date of Patent: Nov. 11, 2003

(54) OPHTHALMOLOGIC APPARATUS AND CONTROL METHOD THEREOF

(75) Inventor: Tetsuji Ogawa, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 3 days.

(21) Appl. No.: 10/022,901

(22) Filed: Dec. 20, 2001

(65) Prior Publication Data
US 2002/0089643 A1 Jul. 11, 2002

(30) Foreign Application Priority Data
Dec. 28, 2000 (JP) ........................................ 2000-400904

(51) Int. Cl.[7] ................................................ A61B 3/14
(52) U.S. Cl. ...................................................... 351/206
(58) Field of Search ................................ 351/202, 203, 351/205, 206, 209, 210, 246; 600/546, 558

(56) References Cited

U.S. PATENT DOCUMENTS

| | | | |
|---|---|---|---|
| 4,595,017 A | * 6/1986 | Semenov et al. | 600/546 |
| 5,212,506 A | * 5/1993 | Yoshimatsu et al. | 351/210 |
| 5,530,494 A | 6/1996 | Ogawa et al. | 351/206 |
| 6,158,864 A | 12/2000 | Masuda et al. | 351/206 |
| 6,327,375 B1 | 12/2001 | Matsumoto et al. | 382/117 |

* cited by examiner

Primary Examiner—George Manuel
(74) Attorney, Agent, or Firm—Fitzpatrick, Cella, Harper & Scinto

(57) ABSTRACT

In an ophthalmologic image pickup apparatus for taking an eye fundus image of an eye to be examined, when an image pickup switch is operated, it is detected whether an image pickup delay switch is operated or not. When it is detected that the image pickup delay switch is operated, light emission of a strobe light source and image pickup of the eye fundus by an image pickup device are delayed. Thus, error image pickup due to nictitation is prevented. Also, when nictitation is detected by a nictitation detector, image pickup of the eye fundus may be similarly delayed.

12 Claims, 8 Drawing Sheets

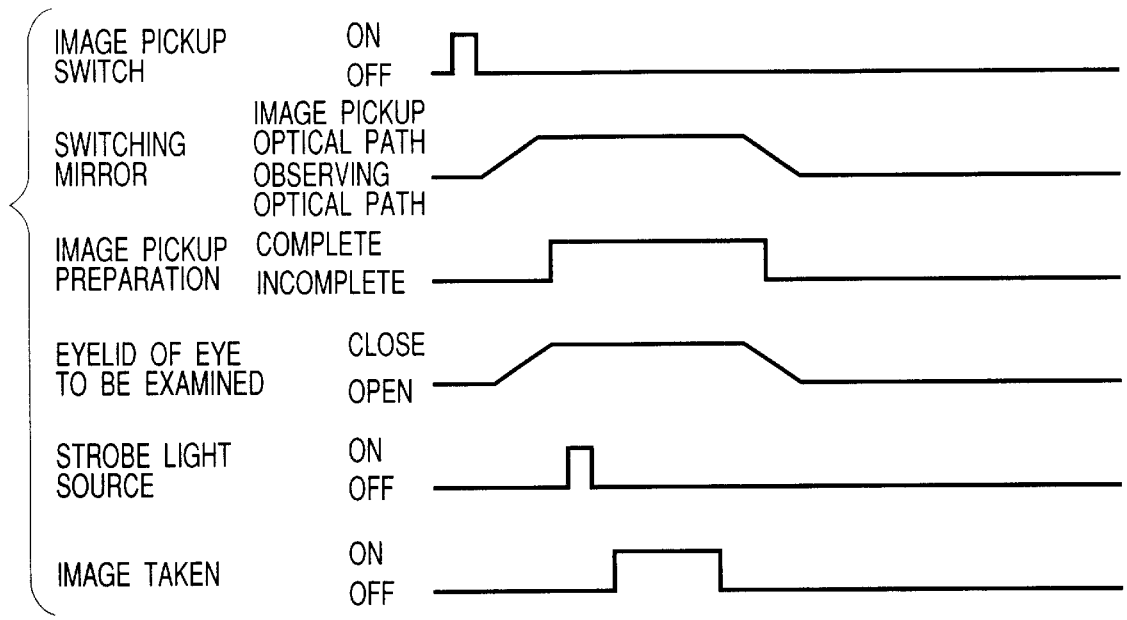
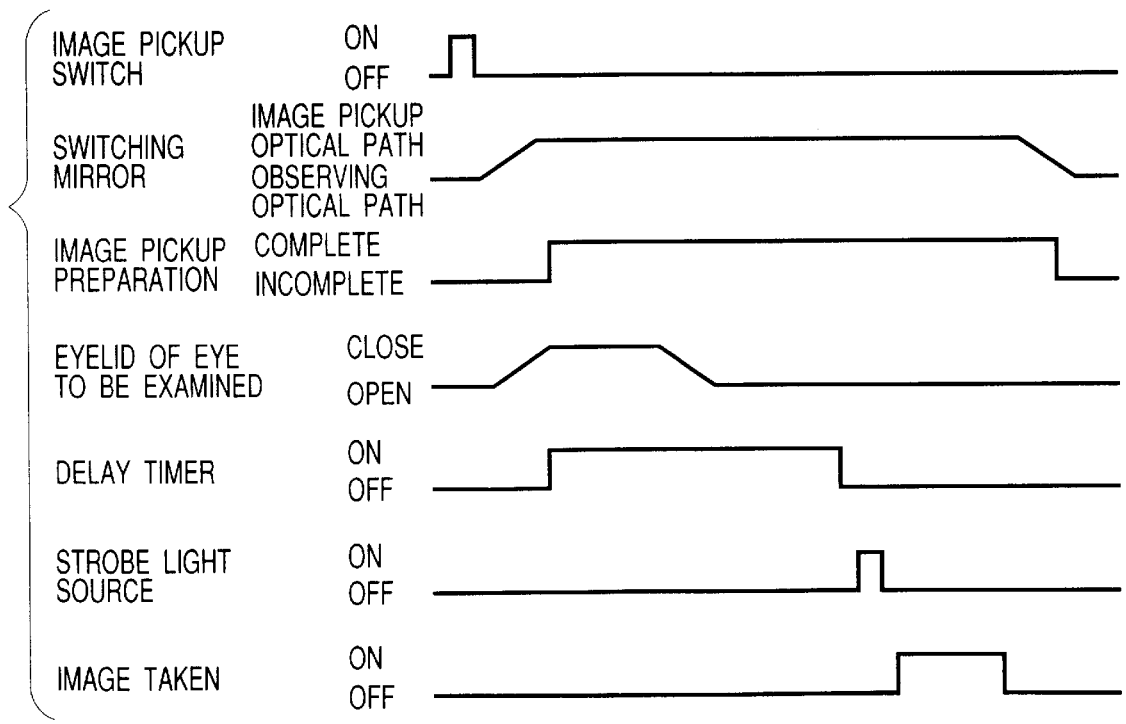

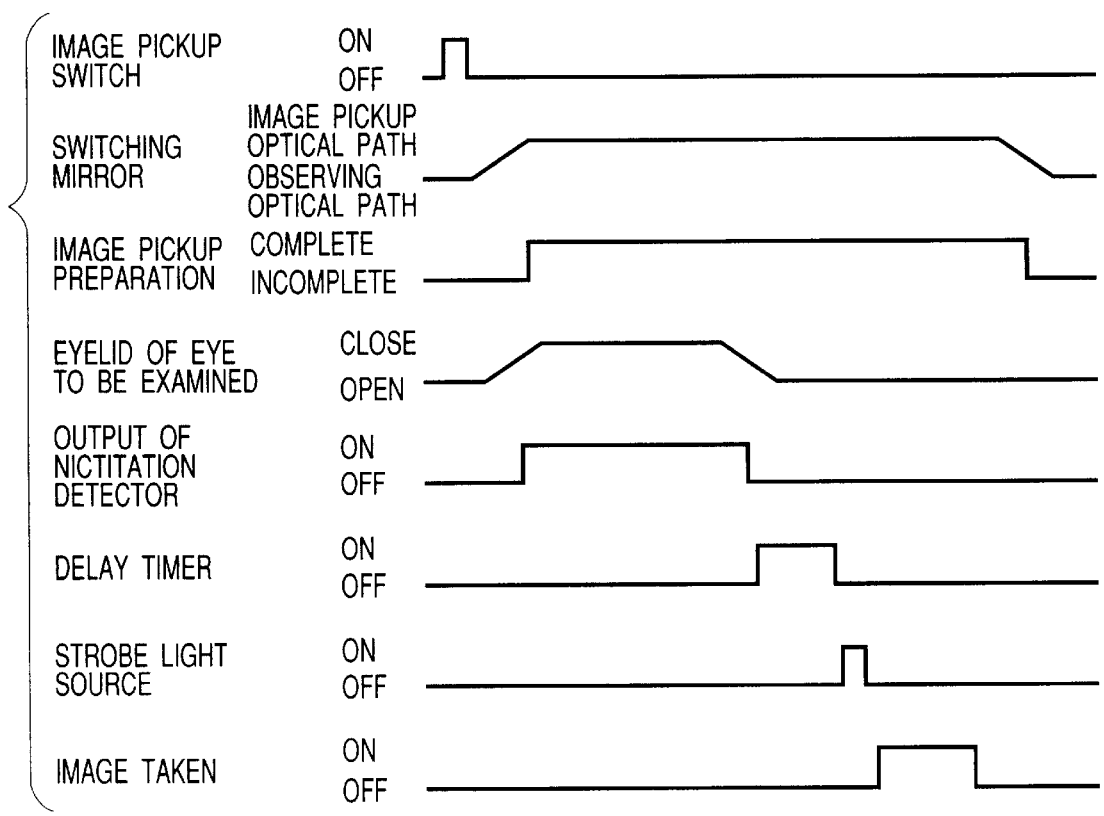

OPHTHALMOLOGIC APPARATUS AND CONTROL METHOD THEREOF

BACKGROUND OF THE INVENTION

1. Field of the Invention

The present invention relates to an ophthalmologic apparatus for taking an ophthalmic image used in an ophthalmologic hospital and the like and a control method thereof.

2. Related Background Art

In a conventional ophthalmologic image pickup apparatus, a nictitation detection function for optically detecting a state of an eyelid in an eye to be examined to detect whether the eye to be examined nictitated or not and for suspending an image pickup operation when the nictitation is produced is known.

However, according to the above nictitation detection function in the conventional example, a nictitation detection operation is performed at predetermined identical timing every time. Thus, in the case of a person to be examined which reacts to, for example, a click sound generated by an image pickup switch or a sound generated by moving an optical member to be inserted onto an optical path in synchronization with image pickup operation and thus unconsciously nictitates, there is a possibility that an image pickup error is continuously caused.

Also, in the case of a detector for detecting the state of an eyelid, it is extremely difficult to accurately determine the state of the eyelid because of an individual difference of reflectance of the eyelid, a difference of the amount of light from an observation light source, an influence of a cilia, and the like. Further, in the case where a special purpose light receiving element is used for detecting the state of an eyelid, when an influences of a cilia and the amount of observation light as described above, and the like are considered in addition to a variation in the sensitivity of the light receiving element, it is difficult to perform a work for adjusting the attachment position.

When the thus attached light receiving element is used, it is further difficult to perform a work for accurately detecting a state in which an eyelid is completely opened after a nictitation is produced. Thus, when the nictitation is detected one time, the image pickup operation must be suspended.

Also, in order to accurately adapt to a variation in the amount of observation light, a method of comparing the amount of incident light with the amount of reflecting light is considered. However, the number of light receiving elements with which the position adjustment is difficult is increased and thus a structure becomes complex and a cost becomes high.

SUMMARY OF THE INVENTION

An object of the present invention is to further improve a conventional ophthalmologic apparatus and to provide an ophthalmologic apparatus having an effect to an eye to be examined which unconsciously reacts to a sound generated by an image pickup operation to produce a nictitation while using an apparatus having a simple and low cost structure and a control method thereof.

Also, another object of the present invention is to provide an ophthalmologic apparatus capable of detecting a nictitation without almost depending on various parameters which influence detection precision by increasing a degree of freedom in an attachment position of a light receiving element and a control method thereof.

In order to attain the above-mentioned object, according to the present invention, there is provided an ophthalmologic apparatus having an image pickup device for taking an image of an eye to be examined and a controller for controlling the image pickup device, characterized in that the controller includes means for performing: a preparation step of detecting a completion of an image pickup preparation operation executed in accordance with an image pickup start signal for starting an image pickup for the image of the eye to be examined; an image obtaining step of obtaining the image of the eye to be examined; and a delay step of adding a delay time before the image obtaining step is started in accordance with a delay execution signal. Further, it is characterized in that the operation of the controller includes means for performing a detection step for detecting a nictitation of an eyelid.

Further objects of the present invention and structures thereof become clear in an explanation of the embodiments described below.

BRIEF DESCRIPTION OF THE DRAWINGS

FIG. 3 is a timing chart of the first embodiment;

FIG. 4 is a timing chart of the first embodiment;

FIG. 9 is a timing chart of the third embodiment.

DESCRIPTION OF THE PREFERRED EMBODIMENTS

The present invention will be described in detail based on embodiments shown in drawings.

Figure 1:
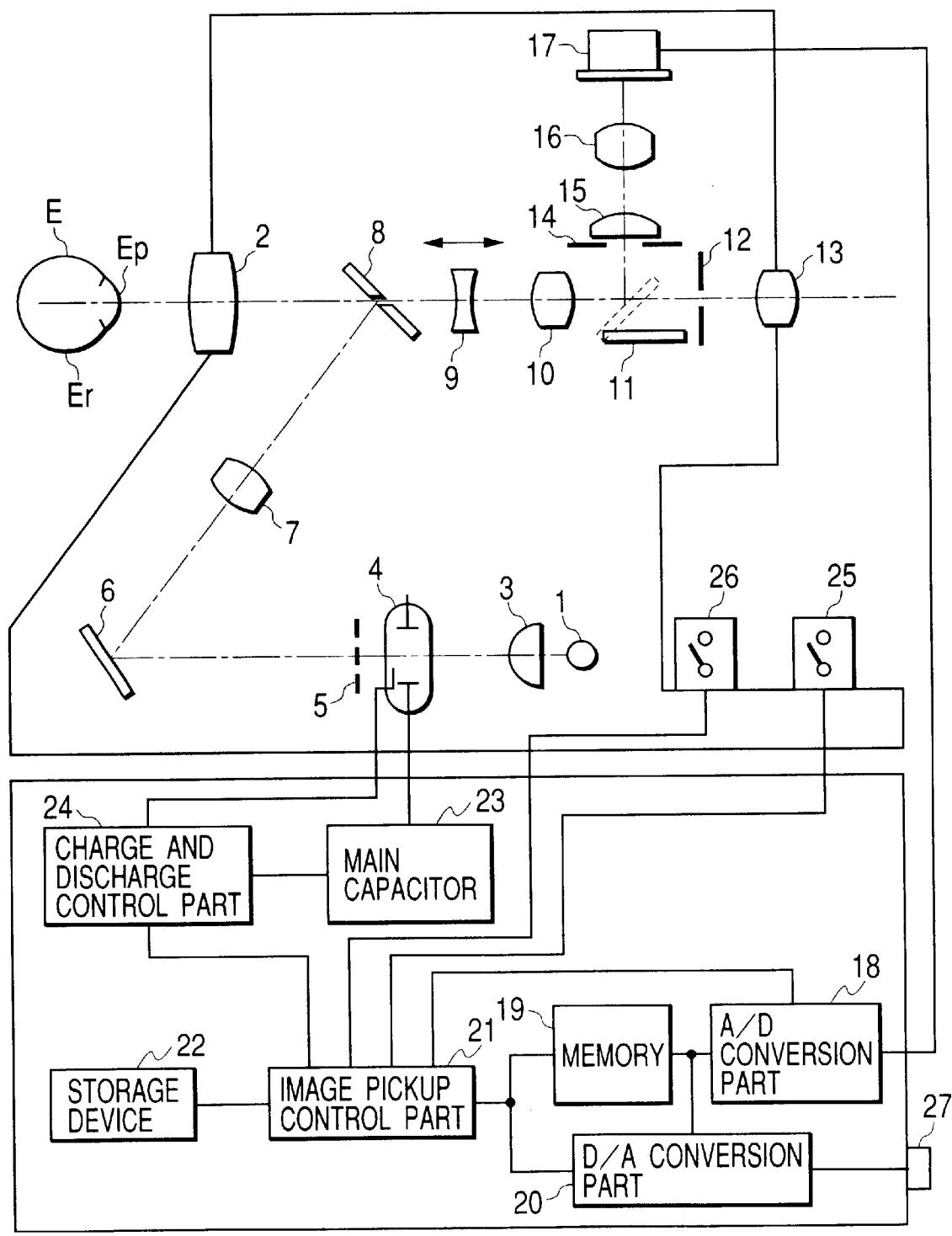
FIG. 1 is a structural view of a first embodiment applied to an eye fundus camera.

FIG. 1 shows a structure of a first embodiment applied to an eye fundus camera. A condenser lens 3, an image pickup strobe light source 4, a ring slit 5, a mirror 6, a relay lens 7, and a hole mirror 8 are arranged in order on an optical path from an observation light source 1 to an objective lens 2 opposite to an eye to be examined E. A focal lens 9, an image pickup lens 10, a switching mirror 11, a field diaphragm 12, and an eyepiece 13 are arranged on an optical path in the back side of the hole mirror 8. When the switching mirror 11 is located in a position indicated by a dotted line on an optical path, an image pickup field diaphragm 14, a field lens 15, an imaging lens 16, and an image pickup device 17 are arranged in order in a reflecting direction of the switching mirror 11.

An output of the image pickup device 17 is connected with a memory 19 and a D/A conversion part 20 through an A/D conversion part 18. The memory 19 temporally stores an A/D conversion result. The A/D conversion part 18, the memory 19, and the D/A conversion part 20 are connected with an image pickup control part 21. The image pickup control part 21 is connected with a storage device 22 such as a magneto-optical disk, a main capacitor 23 for supplying energy to the strobe light source 4, and a charge and discharge control part 24 for controlling energy from the main capacitor 23 and light emission of the strobe light source 4. Further, the image pickup control part 21 is connected with an output of an image pickup switch 25 and an output of a delay execution switch 26. The D/A conversion part 20 is constructed such that an output signal thereof can be outputted to an external monitor through a connector 27.

A light flux emitted from the observation light source 1 is passed through the condenser lens 3 and the ring slit 5, reflected from the mirror 6, passed through the relay lens 7, reflected from the peripheral portion of the hole mirror 8, and passed through the objective lens 2 and a pupil Ep of the eye to be examined E to illuminate an eye fundus Er. Thus, an eye fundus image of the illuminated eye fundus Er is introduced to the eyepiece 13 through the pupil Ep, the objective lens 2, a hole portion of the hole mirror 8, the focal lens 9, the image pickup lens 10, and the field diaphragm 12. The alignment is performed through this observation optical path by an operator.

Figure 2:
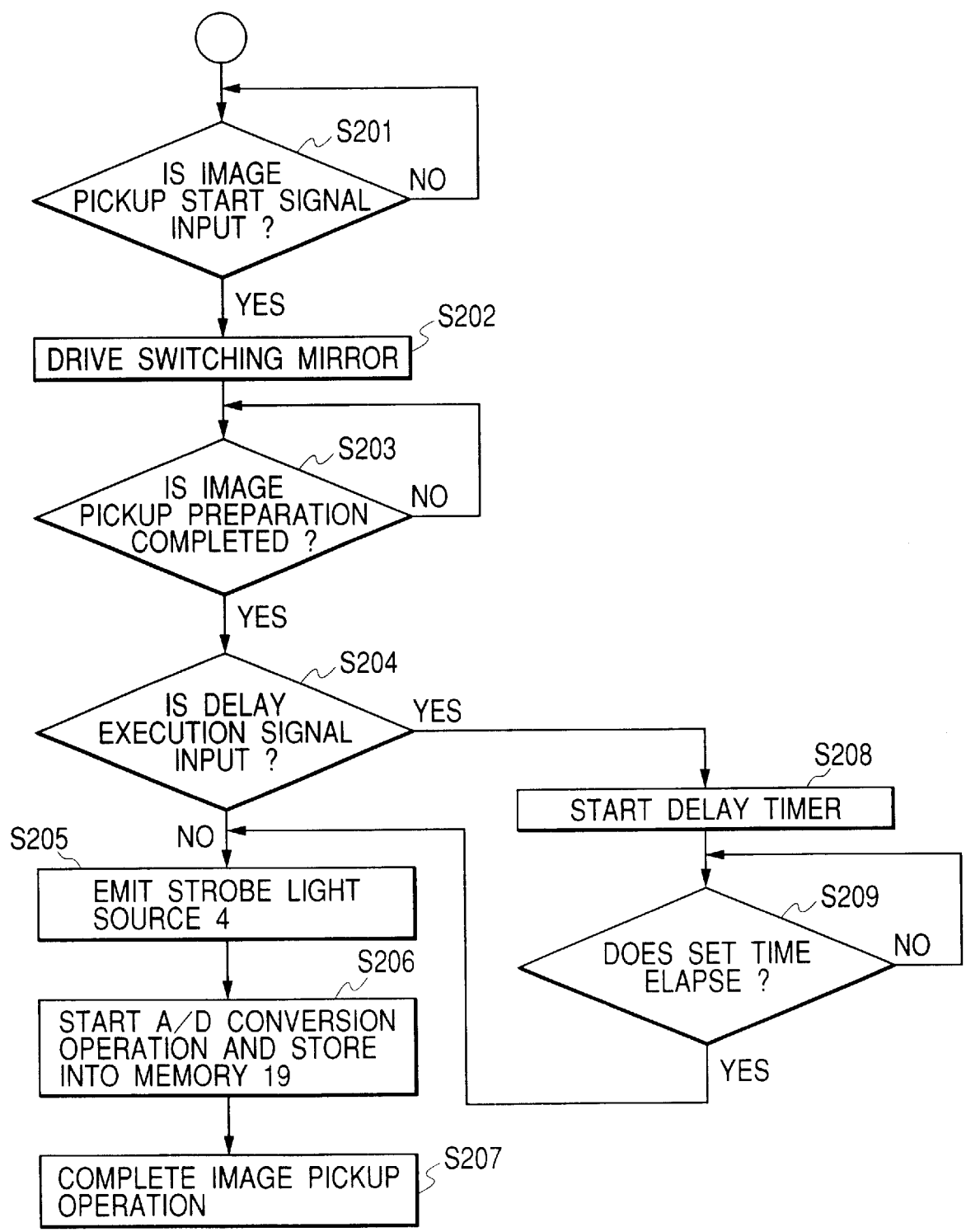
FIG. 2 is a control flow chart of the first embodiment.

FIG. 2 is a flow chart indicating an image pickup control order executed by a program stored in the image pickup control part 21 in the case where image pickup operation is started by an operator. When the alignment is completed and the operator presses the image pickup switch 25, the image pickup control part 21 recognizes a start of image pickup based on an image pickup start signal from the switch 25 in step S201.

Next, the image pickup control part 21 outputs a drive command for the switching mirror 11 in step S202. When the drive command is outputted, the switching mirror 11 is started toward a position indicated by a dotted line by a drive means not shown and the control is transferred to image pickup preparation detection step S203.

In this image pickup preparation detection step S203, it is confirmed that displacement of the switching mirror 11 is completed by a detector not shown. Also, as another structure, determination of whether a shutter located in the front of a film is opened or not in the case where a silver halide emulsion film or the like is used for obtaining an image of the eye to be examined E, determination of displacement in the case where another optical part used for image pickup is moved, and final error determination for the main capacitor 23, the charge and discharge control part 24 and the like may also be included in this image pickup preparation detection step S203. In the case where a device pursuant to an image signal standard such as NTSC is used as the image pickup device 17, when determination of whether an image signal coincides with a vertical synchronizing signal or not is added, the image signal outputted from the image pickup device 17 can be synchronized with image obtaining steps described later.

When the completion of the image pickup preparation is detected in step S 203, the control is transferred to delay selection step S204 for detecting whether the delay execution switch 26 is operated or not. When the delay execution switch 26 is operated, the image pickup control part 21 stores this information and outputs a delay execution signal. Note that, since the operator does not operate the delay execution switch 26 in current image pickup operation, the control is transferred to steps S205 and S206 as image obtaining steps.

A light emission command for the strobe light source 4 is outputted to the charge and discharge control part 24 in step S205 and processing start commands are outputted to the A/D conversion part 18 and the memory 19 in step S206. The charge and discharge control part 24 which receives the light emission command in step S205 provides a light emission trigger to the strobe light source 4. Thus, energy stored in the main capacitor 23 is supplied to the strobe light source 4 to start light emission.

An image pickup light flux is passed through an optical path similar to that for the observation light flux from the ring slit 5 to illuminate the eye fundus Er of the eye to be examined E. The reflected light is reflected from the optical path switching mirror 11 flipped on the optical path and passed through the image pickup field diaphragm 14, the field lens 15, and the imaging lens 16, and thus an eye fundus image is imaged in the image pickup device 17. An image signal obtained by the image pickup device 17 is digitized by the A/D conversion part 18 and temporally written into the memory 19 simultaneously with this digitization. When the A/D conversion and the write into the memory 19 are completed, the image pickup control part 21 recognizes the completion of a series of image pickup and executes post-processing such as returning the switching mirror 11 to an initial position in step S207.

FIG. 3 is a timing chart indicating a series of image pickup operations described above. Here, a person to be examined which reacts to a click sound generated by the image pickup switch 25 or a sound generated by moving the switching mirror 11 and thus unconsciously nictitates is assumed.

As shown in FIG. 3, a person to be examined reacts to a click sound generated by the image pickup switch 25 or a sound generated by moving the switching mirror 11 and starts to close the eyelid. Thus, when the image pickup preparation is completed and the image obtaining steps such as strobe light emission and image taking are performed, the eyelid becomes a complete closed state. When image display operation is performed from an operational part not shown by the operator, while the image pickup control part 21 transfers images stored in the memory 19 to the D/A conversion part 20 in order, D/A output signals are outputted to a monitor not shown through the connector 27. In this operation, the operator recognizes that the image pickup shown in FIG. 3 is an image pickup error due to nictitation and presses the delay execution switch 26. When the delay execution switch 26 is operated, this information is stored in the image pickup control part 21 and the delay execution signal is outputted.

The operator performs the above alignment work and again presses the image pickup switch 25. When the image pickup switch 25 is pressed, the operations from step S201 to step S203 as shown in FIG. 2 are performed as in the case of the above operation. When the completion of the image pickup preparation is detected and the control is transferred to the delay selection step S204, since the delay execution signal is inputted in the current case, the control is transferred to step S208 and the delay steps, steps S208 and S209, are executed. A delay timer is started in step S208. In step S209, the delay is repeated until a preset time is elapsed. When the preset time is elapsed, the control is transferred to step S205 and the above image obtaining steps are executed.

FIG. 4 is a timing chart indicating an image pickup state in the case where the above delay execution switch is operated. Unconscious nictitation of the person to be examined is finished by using the delay timer. Thus, the image obtaining steps are executed with a state in which the eyelid is completely opened. Since unconscious nictitation of the person to be examined is finished after a substantial constant time is elapsed, a delay time preset in the delay timer is preferably registered to be an arbitrary fixed value. In the case of a person to be examined whose nictitation is not finished after such a time is elapsed, a structure is preferably used such that the delay time can be arbitrarily set by the operator. In this case; a structure is used such that the delay time registered by the operator is reflected in step S209. Also, in the case where a device pursuant to an image signal standard such as NTSC is used as the image pickup device 17, the delay time is preferably set to be equal to integer times of the vertical synchronizing signal. Even when the structure is used such that the delay time can be set by the operator, the delay time is preferably made variable based on the vertical synchronizing signal.

In the image pickup operation executed based on the timing chart shown in FIG. 4, as in the above case, a signal is outputted from the D/A conversion part 20 to the external monitor. Also, storage operation into the storage device 22, and the like are performed by judgement of the operator. When such a delay step is provided, the normal image pickup can be easily performed even in the case of the person to be examined which unconsciously nictitates at the time of image pickup.

Figure 5:
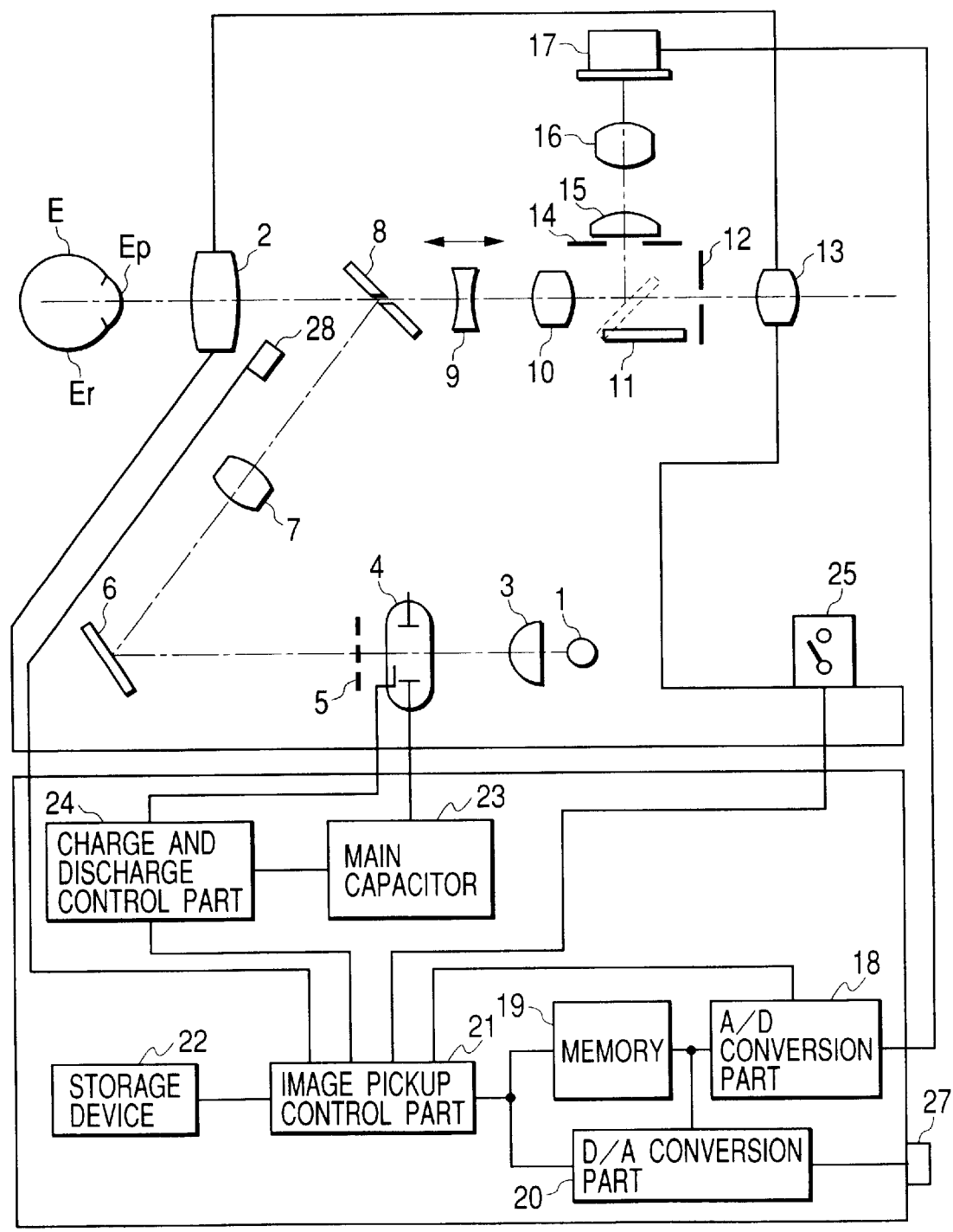
FIG. 5 is a structural view of a second embodiment applied to an eye fundus camera.

FIG. 5 shows a structure of a second embodiment. As compared with the first embodiment, the delay execution switch 26 is deleted and a nictitation detector 28 is slant located behind the objective lens 2 and opposite to a normal direction of the eye to be examined. The nictitation detector 28 in this structure has a light receiving sensor for receiving scattering light scattered in the vicinity of an optical path by closing the eyelid.

Figure 6:
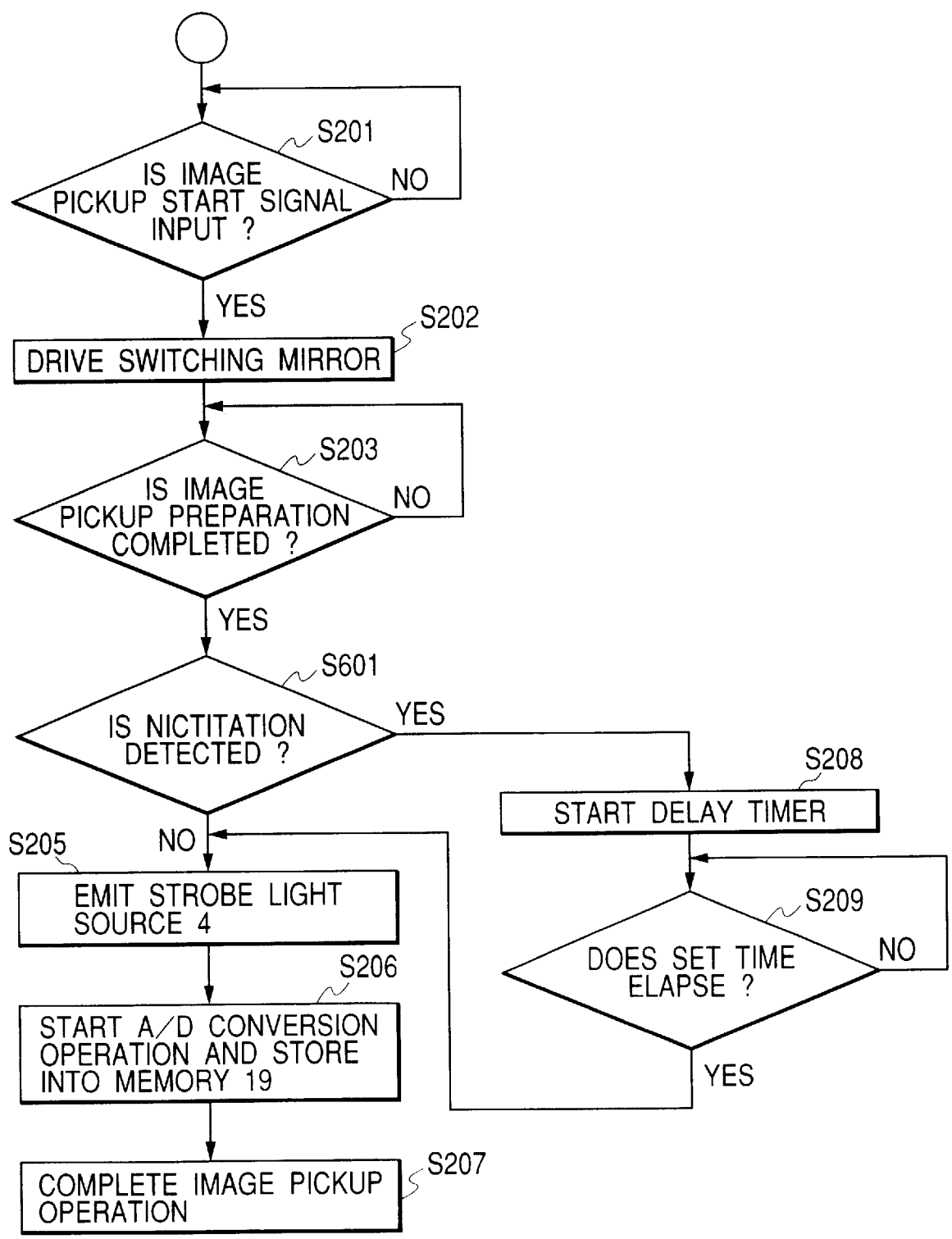
FIG. 6 is a control flow chart of the second embodiment.
Figure 7:
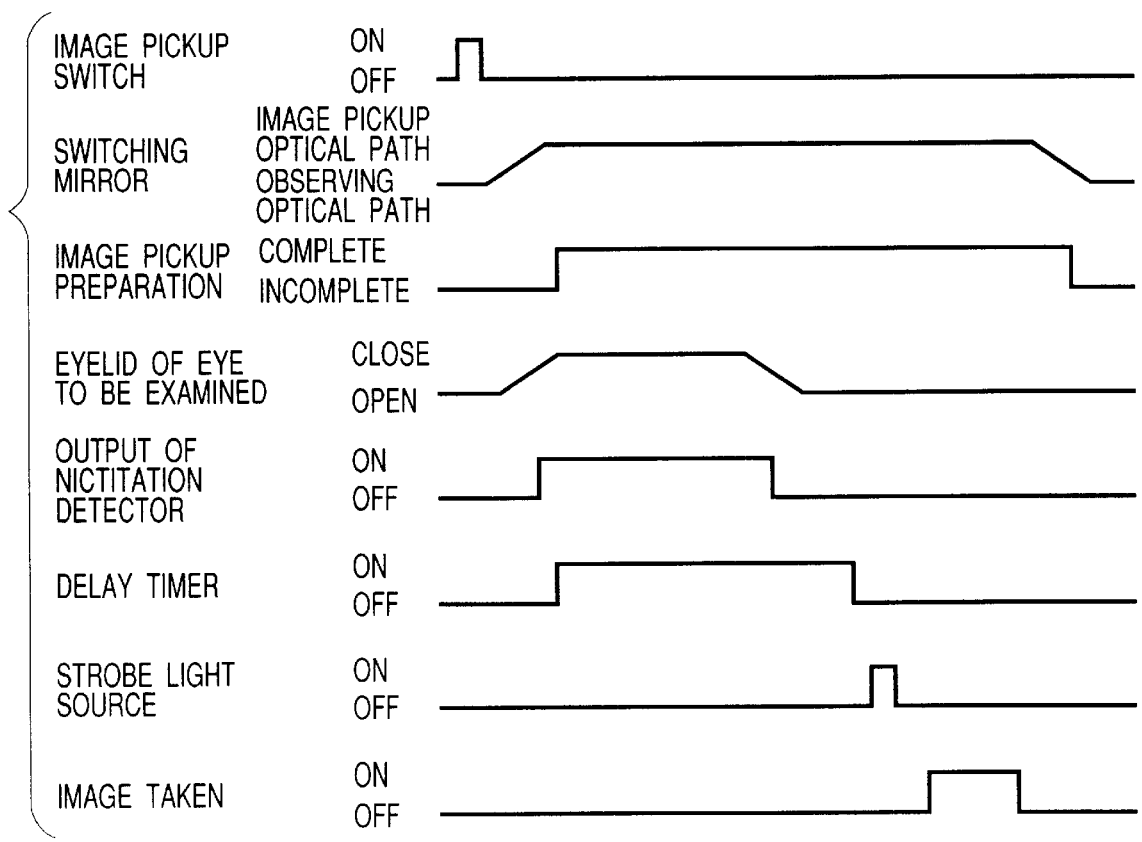
FIG. 7 is a timing chart of the second embodiment.

FIG. 6 is a flow chart in the case where an operator completes the alignment by the above operation and performs image pickup. FIG. 7 is a timing chart indicating timing of the image pickup. As compared with the flow chart of FIG. 2 in the first embodiment, according to FIG. 6, step S204 is deleted and delay selection step S601 is added. When the operator presses the image pickup switch 25, steps S201, S202, and S203 are executed as in the case of the first embodiment, then the switching mirror 11 is driven and an image pickup preparation state is detected.

An output of the nictitation detector 28 is detected in step S601. As shown in FIG. 7, when the image pickup preparation is completed and the output of the nictitation detector 28 is received, the control is transferred to step S208 in FIG. 6 and the delay step is executed as in the case of the first embodiment. After the set time is elapsed, the control is transferred to step S205 and the image obtaining steps are executed. Thus, an image with a state in which the eyelid is completely opened can be obtained as shown in FIG. 7.

As described above, when the nictitation detector 28 and the delay step are provided, it is unnecessary to perform image pickup again even in the case of the person to be examined which unconsciously nictitates at the time of image pickup and normal image pickup can be performed during one image pickup operation.

Figure 8:
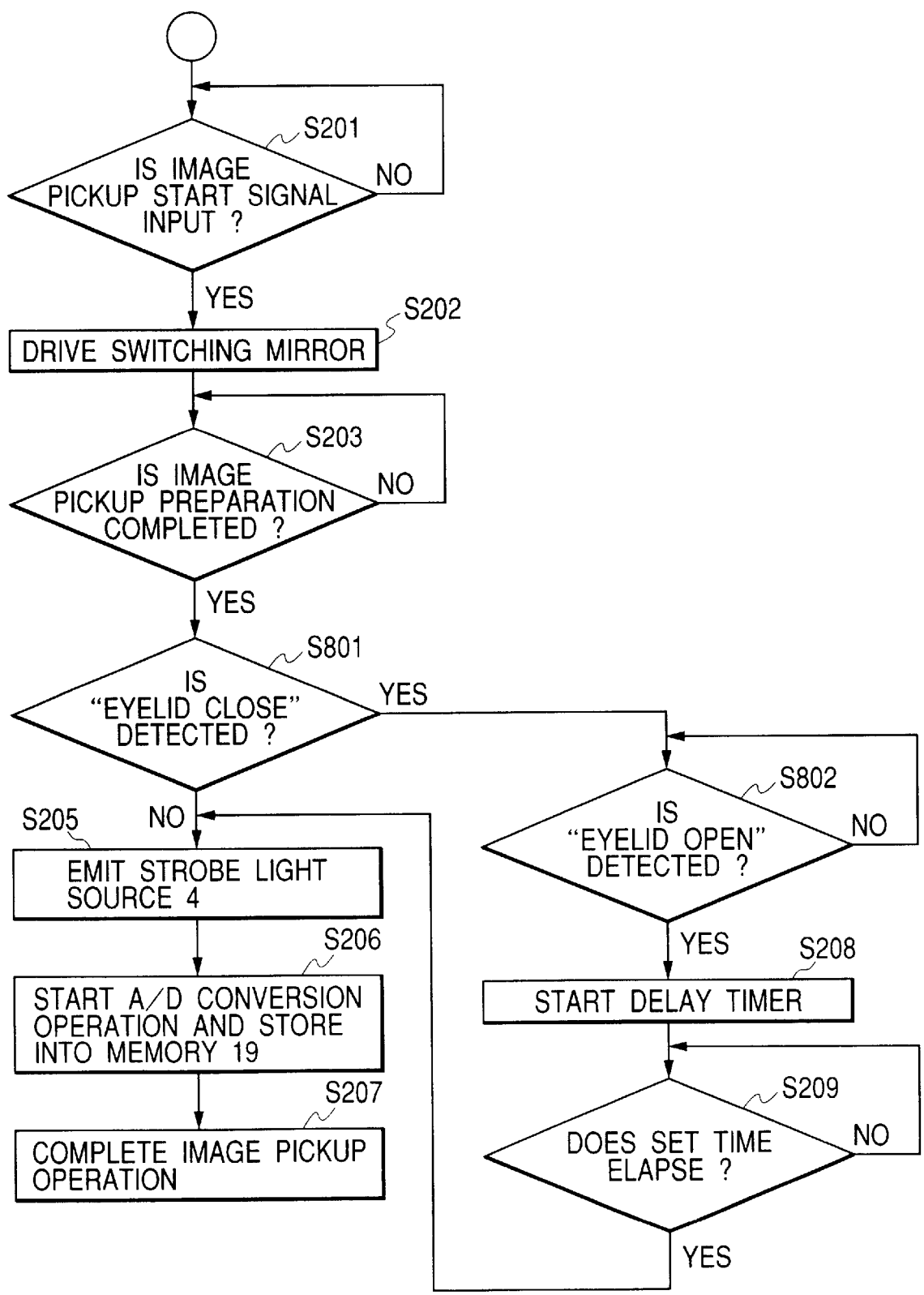
FIG. 8 is a control flow chart of a third embodiment.

FIG. 8 is a flow chart of a third embodiment indicating another processing example using the output of the nictitation detector 28 shown in FIG. 5. FIG. 9 is a timing chart indicating timing of the processing. As compared with the flow chart of FIG. 2 in the first embodiment, according to the flow chart shown in FIG. 8, step S204 is deleted and delay selection steps S801 and S802 are added. When the operator presses the image pickup switch 25, steps S201, S202, and S203 are executed as in the case of the first embodiment, then the switching mirror 11 is driven and an image pickup preparation state is obtained.

In step S801, the output of the nictitation detector 28 is detected. As shown in FIG. 9, when the image pickup preparation is completed and an output "eyelid close" is received from the nictitation detector 28, the control is transferred to step S802 in FIG. 8 and waits until the output of the nictitation detector 28 is changed to an output "eyelid open". When the output is changed to the output "eyelid open", the control is transferred to step S208, the delay steps S208 and S209 are executed as in the case of the first embodiment. Then, the control is transferred to the image obtaining steps S205 and S206.

Here, the following can be read from the timing chart shown in FIG. 9. That is, from an influence of detection precision of the nictitation detector 28, when the output "eyelid open" is received, the actual eyelid of the eye to be examined E is not completely opened. However, when the output signal "eyelid open" is detected in step S802, the control is transferred to the delay steps indicated by steps S208 and S209. After a predetermined time is elapsed, the image obtaining steps are executed. Thus, image pickup is certainly executed without the influence of detection precision of the nictitation detector 28.

Also, when the preset delay time used in the third embodiment is set and registered based on measured data at adjustment before shipment, an error component of an attachment position and an individual difference of a light receiving element can be absorbed. Even in the case where the amount of observation light is small, when a long time capable of sufficiently detecting nictitation is set, a difference of the amount of observation light can be also absorbed. When a delay time is changed to an optimum value for actual use, an individual difference of reflectance of an eyelid, an influence of a cilia, and the like can be also eliminated.

Similarly, in the case where a device pursuant to an image signal standard such as NTSC is used as the image pickup device 17, a timer for measuring a total delay time is started between steps S801 and S802 shown in FIG. 8, it is preferably adjusted in step S209 such that the above delay time condition is satisfied and the total delay time from the completion of the image pickup preparation becomes equal to integer times of the vertical synchronizing signal.

Thus, when two nictitation detection steps for detecting states "eyelid close" and "eyelid open" of the eye to be examined E and the delay steps are provided, an image pickup error due to nictitation can be prevented without depending on the detection precision of the nictitation detector 28 and the like.

According to the above example, when an image pickup error due to nictitation is caused in the last image pickup using a simple apparatus, the delay steps are added. Thus, even in the case of a person to be examined which reacts to a click sound generated by an image pickup switch or a sound generated by moving an optical member to be inserted onto or detached from an optical path and thus unconsciously nictitates, there is no case where an image pickup error is caused in the next image pickup.

Also, it is unnecessary to perform image pickup again even in the case of the person to be examined which unconsciously nictitates at the time of image pickup and normal image pickup without nictitation can be performed during one image pickup operation.

Further, error components of an attachment position precision of a nictitation detector, an individual difference of a light receiving element, a difference of the amount of observation light, an individual difference of reflectance of an eyelid, an influence of a cilia, and the like can be eliminated. Thus, image pickup is certainly executed without suspending image pickup due to nictitation.

As described above, with respect to the ophthalmologic apparatus and the control method thereof according to the present invention, an effect can also be provided to an eye to be examined which unconsciously reacts to a sound generated by an image pickup operation to produce a nictitation while using an apparatus having, for example, a simple and low cost structure. Also, nictitation can be detected without depending on various parameters which influence detection precision by increasing a degree of freedom in an attachment position of a light receiving element.

What is claimed is:

1. An ophthalmologic apparatus having an image pickup device for taking an image of an eye to be examined and a controller for controlling said image pickup device, an operation of said controller comprising:

a preparation step of detecting completion of an image pickup preparation operation executed in accordance with an image pickup start signal for starting an image pickup for the image of the eye to be examined;

an image obtaining step of obtaining the image of the eye to be examined; and a delay step of adding a delay time before the image obtaining step is started, in accordance with a delay execution signal.

2. An ophthalmologic apparatus according to claim 1, wherein the delay step includes a delay setting step of setting the delay time.

3. An ophthalmologic apparatus according to claim 1 or 2, wherein the delay time set by the delay step is based on a synchronizing signal of said image pickup device for taking the image of the eye to be examined.

4. An ophthalmologic apparatus having an image pickup device for taking an image of an eye to be examined and a controller for controlling said image pickup device, an operation of said controller comprising:

a preparation step of detecting completion of an image pickup preparation operation executed in accordance with an image pickup start signal for starting an image pickup for the image of the eye to be examined;

a detection step of detecting a state of an eyelid of the eye to be examined;

an image obtaining step of obtaining the image of the eye to be examined; and a delay step of adding a delay time before the image obtaining step is started, in accordance with a detection by the detection step for detecting the state of the eyelid of the eye to be examined.

5. An ophthalmologic apparatus according to claim 4, wherein the delay step includes a step of setting the delay time.

6. An ophthalmologic apparatus according to claim 4 or 5, wherein the delay time set by the delay step is based on a synchronizing signal of said image pickup device for taking the image of the eye to be examined.

7. A method of controlling an ophthalmologic apparatus having an image pickup device for taking an image of an eye to be examined and a controller for controlling said image pickup device, an operation of said controller comprising:

a preparation step of detecting completion of an image pickup preparation operation executed in accordance with an image pickup start signal for starting an image pickup for the image of the eye to be examined;

a first detection step of detecting a state in which an eyelid of the eye to be examined is closed;

a second detection step of detecting a state in which the eyelid of the eye to be examined is opened;

an image obtaining step of obtaining the image of the eye to be examined; and a delay step of enabling the second detection step in accordance with a detection result by the first detection step and adding a delay time before the image obtaining step is started in accordance with a detection result by the second detection step.

8. A method of controlling an ophthalmologic apparatus according to claim 7, wherein the delay step includes a delay setting step of setting the delay time.

9. A method of controlling an ophthalmologic apparatus according to claim 7 or 8, wherein the delay time produced between the preparation step and the image obtaining step is based on a synchronizing signal of said image pickup device for taking the image of the eye to be examined.

10. An ophthalmologic apparatus for taking an image of an eye to be examined comprising:

image pickup start means for instructing a start of image pickup;

image pickup preparation means for preparing the image pickup in accordance with an operation of said image pickup start means;

image pickup means for performing the image pickup for the eye to be examined in accordance with an operation of said image pickup start means;

image pickup start delaying means for delaying a timing of the start of the image pickup by a predetermined time;

determination means for determining an on state or an off state of said image pickup start delaying means; and control means for performing control so as to start the image pickup after the predetermined time is delayed by the image pickup start delaying means when said determination means determines the on state.

11. An ophthalmologic apparatus for taking an image of an eye to be examined comprising:

image pickup start means for instructing a start of image pickup;

image pickup preparation means for preparing the image pickup in accordance with an operation of said image pickup start means;

image pickup means for performing the image pickup for the eye to be examined in accordance with an operation of said image pickup start means;

image pickup start delaying means for delaying a timing of the start of the image pickup by a predetermined time;

eyelid state detection means for detecting a state of an eyelid of the eye to be examined; and control means for performing control so as to start the image pickup after the predetermined time is delayed by the image pickup start delaying means when the eyelid state detection means detects that the eyelid of the eye to be examined is in a closed state.

12. An ophthalmologic apparatus for taking an image of an eye to be examined comprising:

image pickup start means for instructing a start of image pickup;

image pickup preparation means for preparing the image pickup in accordance with an operation of said image pickup start means;

image pickup means for performing the image pickup for the eye to be examined in accordance with an operation of said image pickup start means;

image pickup start delaying means for delaying a timing of the start of the image pickup by a predetermined time;

eyelid state detection means for detecting a state of an eyelid of the eye to be examined; and control means for performing control so as to start the image pickup after the predetermined time is delayed by the image pickup start delaying means when the eyelid state detection means detects that the eyelid of the eye to be examined is in a closed state and then the eyelid becomes a next opened state.

* * * * *